(12) United States Patent
Nyström et al.

(10) Patent No.: US 8,622,972 B2
(45) Date of Patent: Jan. 7, 2014

(54) PERIPHERAL CATHETER ASSEMBLY AND METHOD OF USING IT

(75) Inventors: Marcus Nyström, Norrahammar (SE); Johan Rinman, Jönkoping (SE); Madelene Eklund, Uppsala (SE)

(73) Assignee: Tradinco AB, Stockholm (SE)

( * ) Notice: Subject to any disclaimer, the term of this patent is extended or adjusted under 35 U.S.C. 154(b) by 621 days.

(21) Appl. No.: 12/182,793

(22) Filed: Jul. 30, 2008

(65) Prior Publication Data
US 2009/0036836 A1 Feb. 5, 2009

Related U.S. Application Data (60) Provisional application No. 60/953,226, filed on Aug. 1, 2007.

(30) Foreign Application Priority Data

Aug. 1, 2007 (EP) .................................... 07113607

(51) Int. Cl.
*A61M 5/178* (2006.01)
(52) U.S. Cl.
USPC .............................. 604/167.03; 604/167.06
(58) Field of Classification Search
USPC ................... 604/164.01–170.03, 180, 533
See application file for complete search history.

(56) References Cited

U.S. PATENT DOCUMENTS

| | | | |
|---|---|---|---|
| 4,929,235 A | 5/1990 | Merry et al. | 604/167 |
| 4,935,010 A | 6/1990 | Cox et al. | 604/122 |
| 5,000,745 A | 3/1991 | Guest et al. | 604/256 |
| 5,041,097 A | 8/1991 | Johnson | 604/167 |
| 5,098,405 A | 3/1992 | Peterson et al. | 604/247 |
| 6,053,861 A * | 4/2000 | Grossi | 600/154 |
| 6,213,978 B1 | 4/2001 | Voyten | 604/164.01 |
| 6,740,063 B2 * | 5/2004 | Lynn | 604/256 |

(Continued)

FOREIGN PATENT DOCUMENTS

DE 20 2007 006 190 U1 9/2007
EP 0 268 480 A1 5/1988

(Continued)

OTHER PUBLICATIONS

European Search Report for EP 07113607.
International Search Report, application No. PCT/EP2008/059950, dated Oct. 10, 2008.

*Primary Examiner* — Kevin C Sirmons
*Assistant Examiner* — Imani Hayman
(74) *Attorney, Agent, or Firm* — Winston & Strawn LLP (57) ABSTRACT

A peripheral catheter assembly having a hollow catheter hub, a female proximal end, a distal end provided with a catheter tube, at least one infusion port located between the distal and proximal ends, a hollow needle module that includes a needle held by a male socket arranged to sealingly engage the female proximal end, and a sealing member engaged inside the catheter hub which serves for facilitating venipuncture without unintended splashing of blood. A sealing valve that includes a septum seal having a weakened portion surrounded by deflectable septum walls, and a hollow tubular extension which protrudes towards a free end from the periphery of the septum seal and extends inside the catheter hub past the infusion port towards the distal end of the catheter hub provide a self-closable sealing member which provide the physician the freedom to leave the patient when the needle module is retracted.

15 Claims, 8 Drawing Sheets

(56) References Cited

U.S. PATENT DOCUMENTS

| | | | |
|---|---|---|---|
| 7,083,598 B2 | 8/2006 | Liska | 604/180 |
| 2001/0005389 A1 | 6/2001 | Iwazaki | 372/29.021 |
| 2002/0058910 A1 | 5/2002 | Hermann et al. | 604/95.04 |
| 2007/0179446 A1 | 8/2007 | Carrez et al. | 604/164.01 |
| 2008/0097344 A1* | 4/2008 | McKinnon et al. | 604/263 |

FOREIGN PATENT DOCUMENTS

| | | |
|---|---|---|
| EP | 0 369 314 A2 | 5/1990 |
| FR | 2 867 081 A1 | 9/2005 |
| WO | WO 2007/028200 A1 | 3/2007 |
| WO | WO 2008/052791 A1 | 5/2008 |

* cited by examiner

PERIPHERAL CATHETER ASSEMBLY AND METHOD OF USING IT

This application claims the benefit of U.S. provisional application No. 60/953,226 filed Aug. 1, 2007, the entire content of which is expressly incorporated herein by reference thereto.

BACKGROUND

The present invention relates to a peripheral catheter assembly of the kind comprising a hollow catheter hub having a female proximal end and a distal end provided with a catheter tube, at least one infusion port located between said distal end and said proximal end, a hollow needle module comprising a needle hold by a male socket arranged to sealingly engage the female proximal end, and a sealing member engaged inside the catheter hub.

Indications for establishing intravenous access using a peripheral vein catheter can e.g. be the needs for administration of liquids, drugs or nutrients or transfusion of blood or blood products. In a peripheral vein catheter a small, flexible tube is used to deliver fluids into the body.

Conventional peripheral vein catheters, which has been used for decades, for example a Venflon™ obtainable from Becton Dickinson Infusion Therapy, Helsingborg, Sweden, comprise a hollow main body with a female end plug accommodating a needle hub with a male socket carrying a puncture needle for inserting a catheter into the vein, usually in the back of the hand or in the forearm. A common Venflon™ has an infusion port perpendicular to the main body. The infusion port is fluid sealed from the main body simply by means of a short piece of an axially compressible, hollow tube inserted inside the main body just below the infusion port. The skilled person is aware that a major disadvantage and annoyance is that the tube is hollow along the entire length, with the result that when the puncture needle is removed, blood is able to flow freely out of the open female end of the main body. The only remedy is to establish stasis to slow or stop this blood flow by compressing the penetrated vein with a finger on one hand while struggling with the other hand to quickly plug in an external device, such as e.g. a male luer connector connected to a drip. Even though, it is difficult to avoid minor blood loss and blood splashing. Moreover, during this awkward procedure the physician needs to have all remedies, including substitute remedies, within reach before puncture because he cannot leave the patient.

From US 2001/005389 is known an over-the-needle catheter comprising a hub without infusion port. The hub is permanently equipped with a sharp pointed cannula, in the same manner as a trocar. A T-shaped septum seal is mounted on the end of a metal tube, which is firmly fixed inside the hub. The T-shaped septum seal consists of a shank, i.e. a short, narrow tubular portion, and a head portion with a small central weakened portion. The T-shaped septum seal is slidably arranged on the metal tube, causing the metal tube to penetrate the weakened portion and open a permanent flow path through the bores of the cannula and the metal tube upon forward movement of the T-shaped septum seal towards the cannula. A conical male luer connector may be used for pushing the T-shaped septum seal forward to provide permanently and irreversibly penetration of the weakened portion. However, a disadvantage of this design is that if the male luer connector is disconnected the T-shaped septum seal cannot close again and the flow passage is open. Furthermore, the thin shank of the T-shaped septum seal has no sealing capacity. This shank only serves as a guide and mounting member when pushing the T-shaped septum seal along the axial length of the metal tube, and the T-shaped septum seal cannot be retracted once it has been pushed forward.

U.S. Pat. No. 5,041,097 describes an intravenous catheter with a protective end seal at the connection end for preventing fluid leakage during installation, connection, and use. A thin membrane seal formed of resilient, stretchable material is secured over the opening at the exterior surface of the rear end of the catheter base. In the assembled and packaged condition a needle with a bevelled front end is installed in the catheter. The bevelled front end of the needle is pushed through the membrane seal to puncture the membrane seal, which seal is stretched as the forward motion of the needle continues, and conforms to the profile of the needle base and allow it to engage the interior of the catheter base. When the needle is retracted, it is intended that the membrane seal revert to its start condition. A male luer connector can be installed in the base in a similar forceably manner. Both the needle base and the male luer connector must expand the small puncture hole in the stretchable membrane considerably to create sufficient bulk space for the base or connector. However, the major force which is required to allow this entails a considerable risk that the membrane seal either bursts or is pulled out of its attachment. In both cases the membrane seal is unable to close the flow path through the base again if e.g. the male luer connector is disconnected. Moreover, the elastic membrane seal is susceptible to be detached from the base when subjected to the pushing forward force. Thus, improvements in these type devices are needed.

SUMMARY OF THE INVENTION

In a first aspect is provided a peripheral vein catheter assembly that remedies the disadvantages and shortcomings of the prior art peripheral vein catheters.

In a second aspect is provided a peripheral vein catheter assembly which self-closes the flow path when the needle is removed after venipuncture, and opens a flow path in response to introduction of a male part in the catheter hub.

In a third aspect is provided a sealing valve which can be implemented in a conventional catheter hub with an infusion port.

Within the context of the present application a septum seal is to be understood as a flexible, fluid-tight, sealing structure which divides a hollow structure, such as the bore of a catheter hub, into two hollow sections adjacent each other and separated by the septum seal.

The novel and unique whereby this is achieved according to the present invention is the fact that the sealing member is a sealing valve comprising a septum seal having a weakened portion surrounded by deflectable septum walls. The sealing valve also has a hollow tubular extension, which protrudes towards a free end from the periphery of the septum seal and extends inside the catheter hub past the infusion port towards the distal end of the catheter hub.

The septum seal completely closes and seals the female proximal end of the hollow catheter hub. This prevents blood from emerging from the catheter hub when after venipuncture and the risk of an air embolism is substantially reduced or even eliminated.

The weakened portion of the deflectable septum wall allows this wall to be penetrated by the needle without substantially impact on the surrounding deflectable wall. Once the penetrating object, whether it is the needle or a more bulky male part, is removed the sealing valve self-closes. When a wider or more bulky object, such as a male luer connector or the male socket, is introduced to engage the female proximal end of the hollow catheter hub the interior of the hollow tubular extension adjacent the female proximal end advantageously serves for receiving the deflected septum seal wall. The tubular extension sealingly engages the interior wall of the catheter hub at the section of the tubular extension, which extends past and below the infusion port. As a result, the sealing valve seals both the entrances, i.e. both the female proximal end of the catheter hub and the infusion port. Due to the hollowness of the tubular extension the circumferential wall of the tubular extension is able to yield in response to an infusion fluid, which is forceably injected through the infusion port, to thereby allow the infusion fluid to flow further into the vein.

The catheter hub may advantageously be provided with an annular relief for at least partly receiving the deflected septum seal wall and/or a part of the wall of the tubular extension displaced by the deflected septum seal wall when e.g. a male luer connector or the male socket is introduced through the weakened portion of the septum seal. The deflected septum seal wall easily conforms around the introduced object and serves together with the wall of the tubular extension as a combined sealant between the object and the interior wall of the catheter hub.

In a preferred embodiment at least the tubular extension may be provided with at least one securing means for firmly securing the sealing valve inside the catheter hub to prevent axial and/or rotational displacement of the sealing valve inside the catheter hub. Additionally, the septum seal can be provided with securing means.

Various kinds of securing means may be for foreseen within the scope of the present invention and combinations of these may be used.

In a very simple embodiment the securing means can just be an adhesive substance such as glue, which additionally may provide sealing. In case an adhesive substance is used to secure the tubular extension, only the part of the tubular extension adjacent the septum seal may be adhered to the interior of the catheter hub. At least a part of the length of the tubular extension that extends past and below the infusion port is left free of glue to allow unobstructed compression of the tubular extension in response to infusion of an infusion fluid through the infusion port.

Alternatively or additionally the securing means may comprise a circumferential sealing rib and one or more anchoring ribs extending in the axial direction of the tubular extension between the septum seal and the circumferential sealing rib, which ribs are forced fitted into engagement with the proximal end of the catheter hub. Preferably, the ribs may be forced fitted into complementary shaped grooves provided in the wall of the catheter hub.

In yet an alternative embodiment the ribs may be provided on the inside of the catheter hub and the grooves may be provided on the tubular extension. This embodiment leaves less space for receiving the deflected wall of the septum membrane when a male socket or male luer connector is inserted into the female proximal end of the catheter hub resulting in a very reliable docking of the male part. Hence, this embodiment has minimum susceptibility to accidental disconnection of the male connector.

For additional securing of the sealing valve a glue can be provided in the spaces between the ribs. Such glue can in an easy manner be injected through small holes through the wall of the catheter hub, which holes may self-seal by means of the surplus of injected glue.

In yet an alternative embodiment proper dimensioning of internal diameters of the hub to be equal to or smaller than the external diameters of the septum seal and the tubular extension may provide sufficient securing due to press fitting.

In order for the deflectable wall to be able to deflect to allow entrance of a male part, such as a male socket or male luer connector, and provide adequate sealing between the catheter hub and the male part, the weakened portion may be designed as a notch extending crosswise of the septum seal. A notch allows the weakened portion to split apart without pushing the sealing valve further inside the catheter hub.

Optionally, a hollow annular locking member having a first end face facing the septum seal and an opposing second free end face with an opening for receiving a male socket or a male luer connector may advantageously absorb the forces on the septum seal resulting from the longitudinal axial introduction of the male socket or male luer connector into the female proximal end of the catheter hub. The locking member then serves as a brake to avoid unintentional damage to the peripheral catheter assembly, such as unintentional rupture of the weakened portion or displacement of the sealing valve resulting in lack of sealing capability at the infusion port or at the female proximal end of the catheter hub. Preferably the first end face abuts the septum seal, but the male socket may in some embodiments be so long that the weakened portion is preliminary divided into the deflectable wall part. In this case the sealing valve is made of a material of a great elastic memory to maintain the self-closing capability when the male socket is retracted.

In the preferred embodiment the hollow annular locking member may have a bore, which tapers towards the first end face of the locking member. This conic bore advantageously prevents the male socket or male luer connector from being inserted too far into the female proximal end of the catheter hub and thereby guards against unintentional or too early rupture of the weakened portion. The tapered bore of the annular locking member further serves to guide the male socket or male luer connector into engagement with the female proximal end of the catheter hub.

The catheter hub may be provided with an attachment member for enabling easy attachment of the peripheral catheter assembly to a subjacent surface, such as the patient skin above the punctured vein.

In a preferred embodiment the attachment member may be united with a plaster member for adhering the peripheral catheter assembly to a subjacent surface, e.g. as described in the inventors own U.S. Pat. No. 7,083,598. It may be preferred that the plaster member has an aperture for passage of at least the catheter tube, however within the scope of the present invention the plaster member may quite as well be a thin penetratable adhesive support sheet without any premade aperture for the catheter tube and needle, in which case said tube and needle first is inserted in their advanced position in the catheter hub at the time of venipuncture.

To provide the physician or nurse with the opportunity to make visible ascertainment of successful venipuncture at least the catheter hub may be transparent.

The invention also relates to a method of using the peripheral catheter assembly described above. The method comprises the steps of folding the part of the plaster member covering the catheter tube back to view the pointed end of the needle, puncturing the vein, advancing the catheter tube into the vein while gradually retracting the needle module until the needle is fully retracted and the septum seal has self-closed, adhering the plaster to the skin of the patient, establishing fluid connection between the vein and the exterior by inserting a male part connector through the septum seal.

BRIEF DESCRIPTION OF THE DRAWINGS

The invention will be explained in greater detail below, describing only exemplary embodiments with reference to the drawing, in which.

DETAILED DESCRIPTION OF THE PREFERRED EMBODIMENTS

In the following the invention is described by way of example on the assumption that the peripheral catheter assembly is used for a venipuncture. However, the peripheral catheter assembly can also be used for other kinds of punctures requiring introduction of a small catheter in a tubular organ. For example the peripheral catheter assembly with a sealing valve according to the present invention can advantageously be used for accessing the pleural space in order to withdraw pleural effusions without air entering the pleural space due to the negative pressure which is build up during inspiration.

Figure 1:
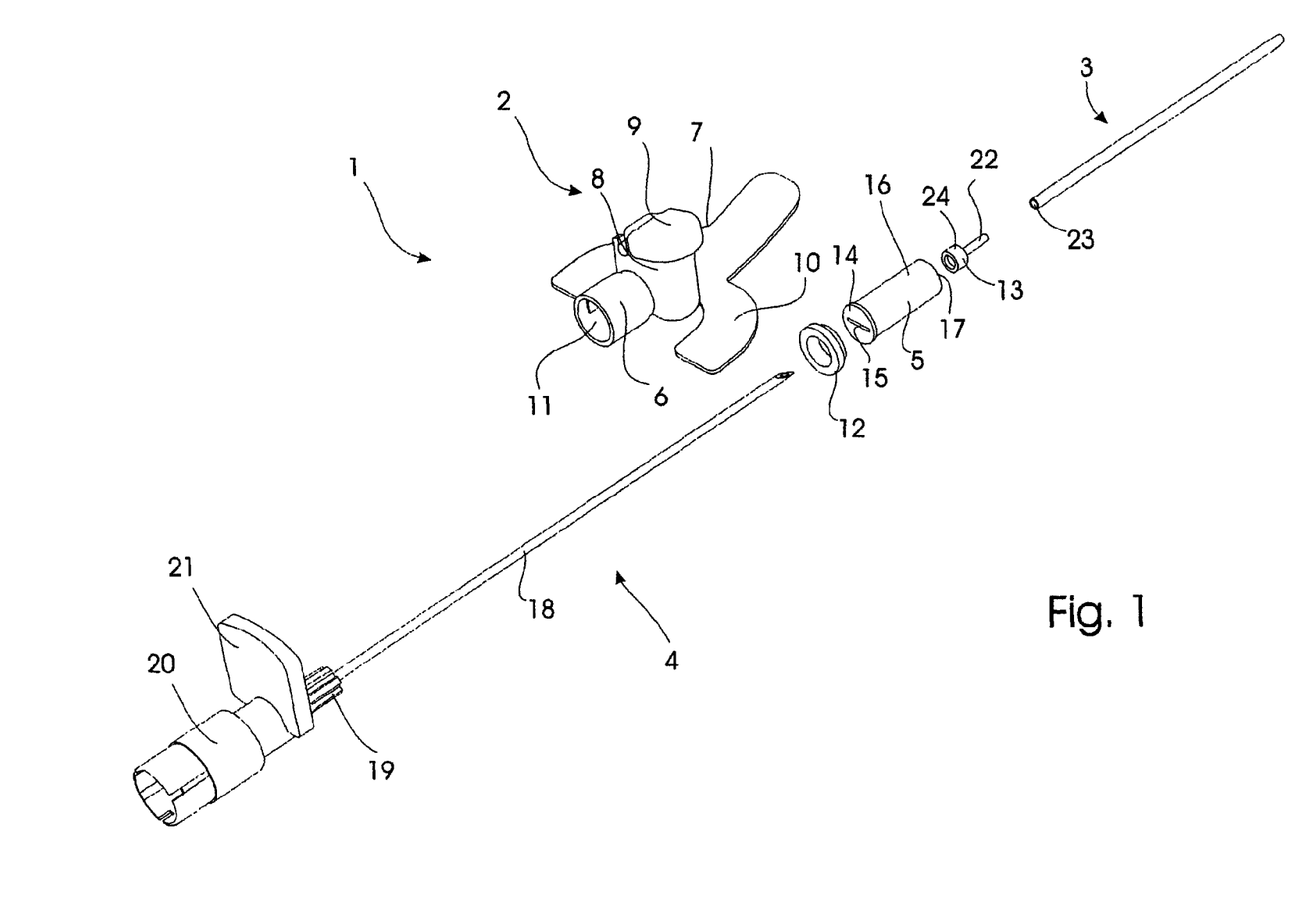
FIG. 1 shows an exploded view, seen in perspective, of a first embodiment of a peripheral catheter assembly according to the present invention.

The first embodiment for a peripheral catheter assembly, which is designated in its entirety with the reference numeral 1, consists of a hollow catheter hub 2, a flexible catheter tube 3, a needle module 4 and a valve sealing 5, which fits into the catheter hub 2. Both the catheter tube 3, which e.g. may be of flexible polyurethane (PU), Fluorinated Ethylene Propylene copolymer FEP or poly vinyl chloride (PVC) or other suitable polymer, and the needle module 4 are known to the person skilled in the art and of substantially conventional general design.

The hollow catheter hub 2 has a female proximal end 6 for plugging in a complementarily shaped male part, and a tapering distal end 7. An infusion port 8, a "chimney", merges perpendicularly into the hollow catheter hub 2 to allow fluid communication between the bore 11 of the hollow catheter hub 2 and the infusion port 8, however any angular relationship between the catheter hub 2 and the infusion port 8 is intended within the scope of the present invention. The infusion port 8 is shown to be closed by a pivotable flap lid 9 but closure means such as membranes or plugs are suitable alternatives. A Y-shaped attachment member 10 protrudes from the catheter hub 2 to provide an enlarged, flat attachment area and surface for the catheter hub 2 when the peripheral catheter assembly 1 is secured to the patients skin. The Y-shaped attachment member 10 can be combined with the catheter hub 2 using various means, such as adhesive substances, in particular a glue, or be moulded together with the catheter hub 2 in one single process, such as injection moulding.

The valve sealing 5 fits intimately into the bore 11 of the catheter hub 2 between the female proximal end 6 and the distal end 7 and is, in the case shown, arranged between an annular locking ring 12 at the female proximal end and a connection piece 13 for the catheter tube 3 at the distal end 7. The sealing valve 5 consist of a septum seal 14 with a notch 15 and a hollow tubular extension 16 which protrudes from the septum seal 14 towards a free end 17. Both the annular locking ring 12 and the connection piece 13 can be dispensed with. For example the catheter tube 3 can be secured directly to the distal end, or even be moulded in the same process. The annular locking ring 12 can alternatively be made as an annular extension of the sealing valve. Various embodiments of sealing valves is shown and described in relation to FIGS. 6a,b,c.

The needle module 4 is an obturator module consisting of a hollow needle 18, mounted in a knurled male socket 19 on a female plug 20, which may or may not provide for fluid communication between the vein and the exterior environment when fully inserted into the catheter hub 2. In case fluid communication is not intended the female plug 20 is closed either by means of a removable plug or a permanent closure. In case fluid communication is intended the female plug 20 is hollow, allowing fluid communication through needle 18, male socket 19 and female plug 20. The cannula 18 has an upright finger press tab 21 that aids the physician in applying a controlled penetration and insertion force to the cannula 18 and serves as a grip 21 when the needle hub 4 is retracted. Although the male socket is shown to be knurled, a conventional male socket 19 having a smooth surface may also be used.

Figure 2:
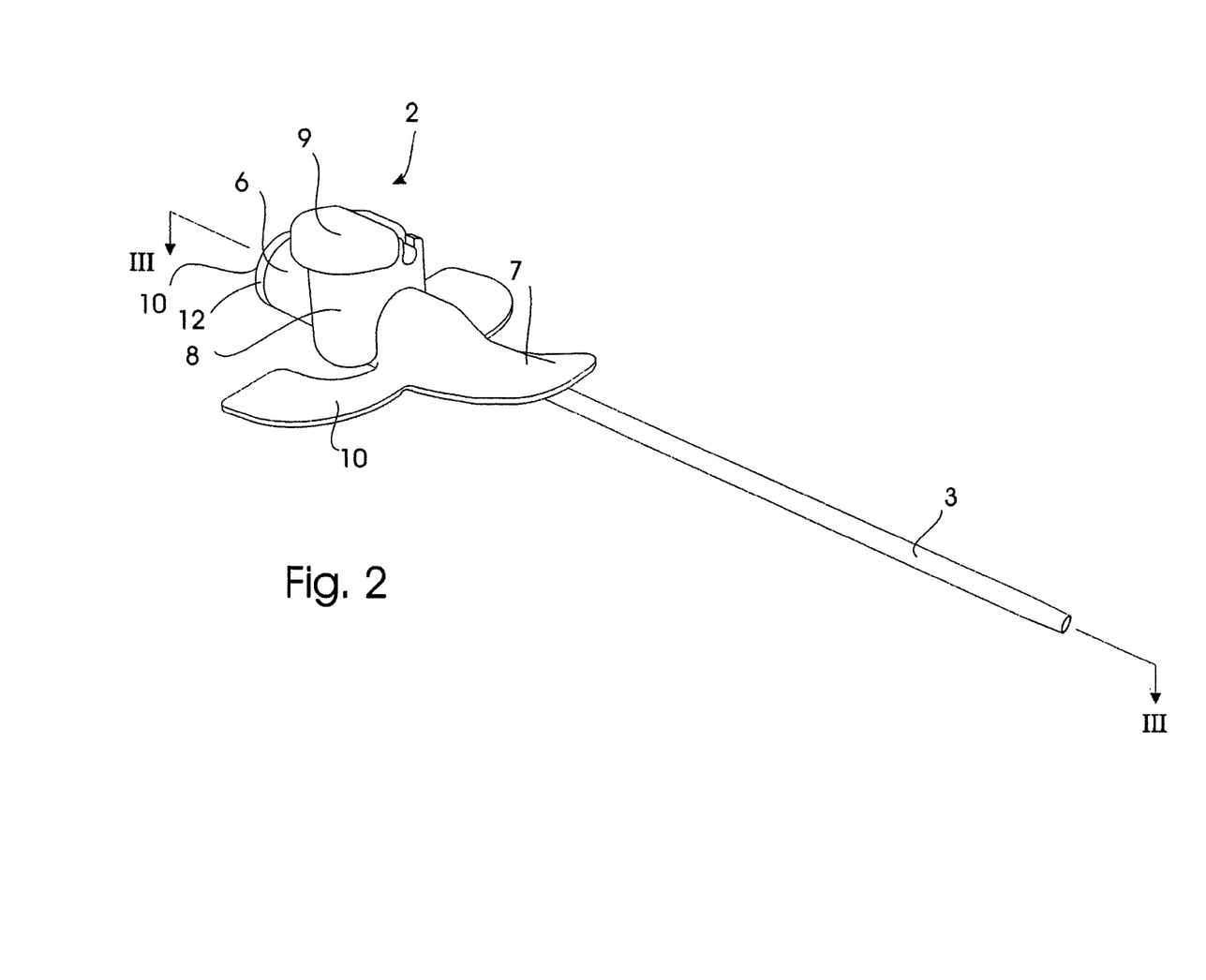
FIG. 2 shows the device of FIG. 1 in an assembled state without the needle module.

FIG. 2 shows, seen in perspective, oblique from the top of the infusion port 8, the catheter hub 2 provided with the catheter tube 3.

Figure 3:
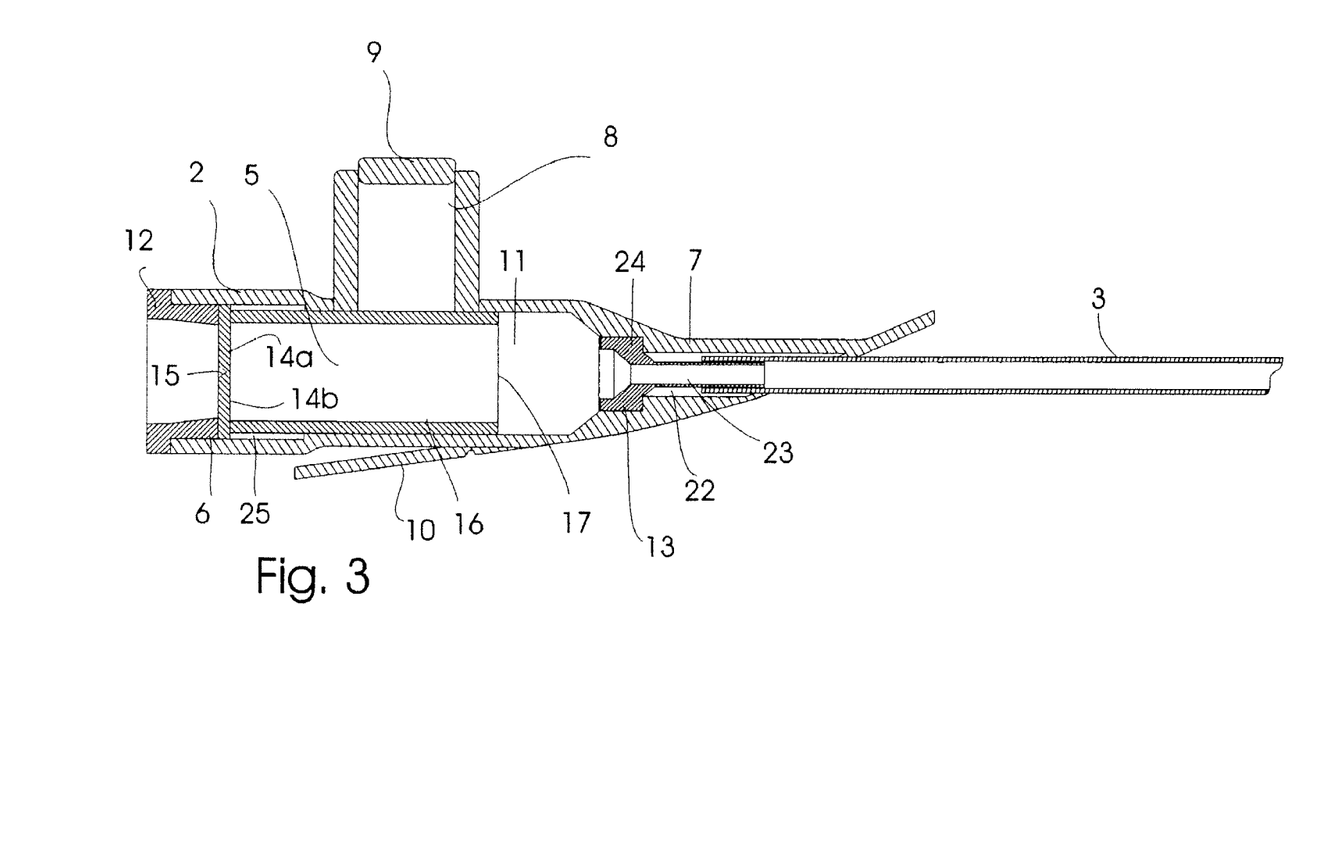
FIG. 3 shows an axial sectional view taken along the line III-III of FIG. 2.

As seen more clearly in the axial sectional view of FIG. 3, which is taken along line III-III in FIG. 2, the sealing valve 5 is mounted inside the bore 11 of the catheter hub 2, between the annular locking ring 12, which is inserted in the female proximate end 6 of the catheter hub 2, and the connection piece 13, which is inserted in the distal tapering end 7 of the catheter tube 3. The connection piece 13 has a neck part 22 and a head part 24 both of which are mounted inside the tapering distal end 7 of the catheter hub 2. The head part 24 has a larger diameter than the diameter of the outlet opening of the distal end 7 of the catheter hub. As a result of different diameters the connection piece 13 cannot be forced out of the distale end 7 of the catheter hub 2 upon manoeuvring the needle module 4. The exterior diameter of the neck section 22 is selected to correspond to or to be slightly larger than the diameter of the bore 23 of the catheter tube 3 to ensure firm engagement of the catheter tube 3 and secure attachment of the catheter tube 3 to the catheter hub 2.

The female proximal end 6 of the catheter hub 2 has an internal annular relief 25 for receiving divided, deflected septum wall parts 14a,14b in response to introduction of a male socket 19, as disclosed and described in more detail with reference to FIG. 4. and FIG. 5.

Figure 4:
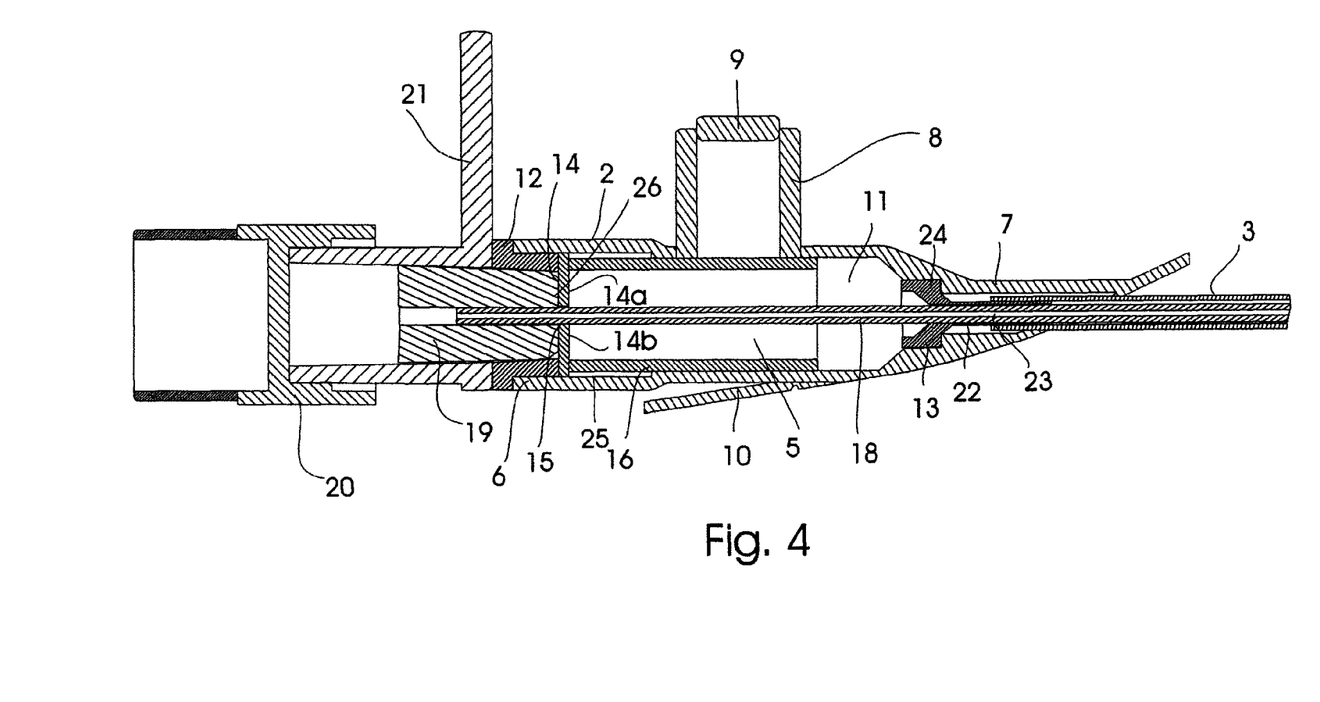
FIG. 4 shows the device of FIG. 1 provided with the needle assembly module ready for venipuncture.

FIG. 4 shows the needle module mounted with the male socket 19 inserted into the female proximal end 6 of the catheter hub 2. The male socket 19 abuts the septum seal 14 with a front end 26. The needle 18 has penetrated the notch 15 without substantially affecting or deflecting the septum seal 14 of the sealing valve 5. Once venipuncture has taken place the needle 18 is retracted and the septum seal wall 14a, 14b self-closes to prevent blood backflow.

Figure 5:
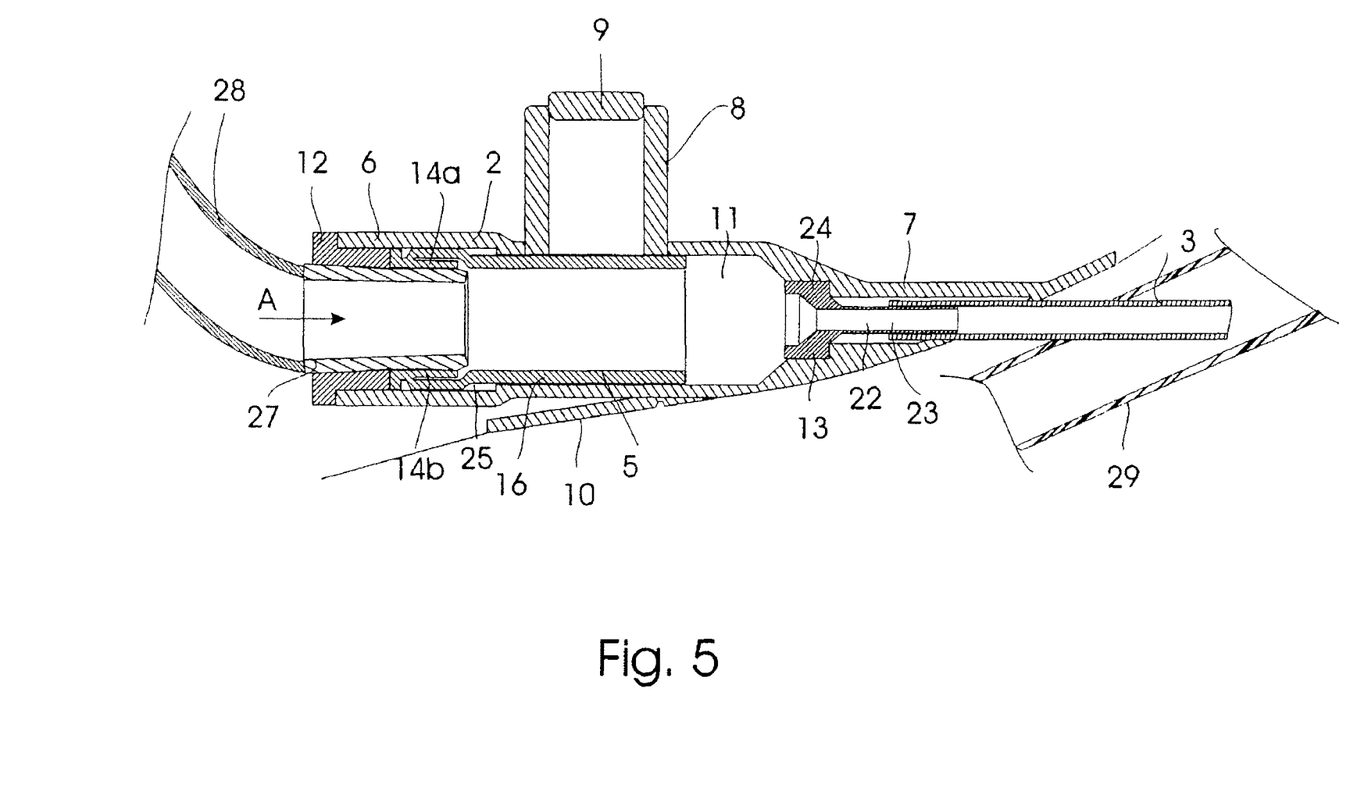
FIG. 5 shows the device of FIG. 1 where the needle assembly module is retracted and a male luer connector is inserted ready to provide fluid infusion to a patient, FIGS. 6a,b, and c are perspective views of various embodiments of sealing valves which may be used in the present peripheral catheter assembly.

In FIG. 5 the male socket 19 has been retracted. A conical male luer connector 27 with a medical tube 28 is, guided by the annular locking ring 12, forceably inserted into the female proximal end 6 of the catheter hub 2. The walls 14a,14b of the septum seal 14 has been manually forced away from each other and pressed into the annular relief 25 of female proximal end 6 of the catheter hub 2 to provide fluid communication between a liquid reservoir (not shown) and the vein 29 as indicated by the arrow A.

Figure 6A:
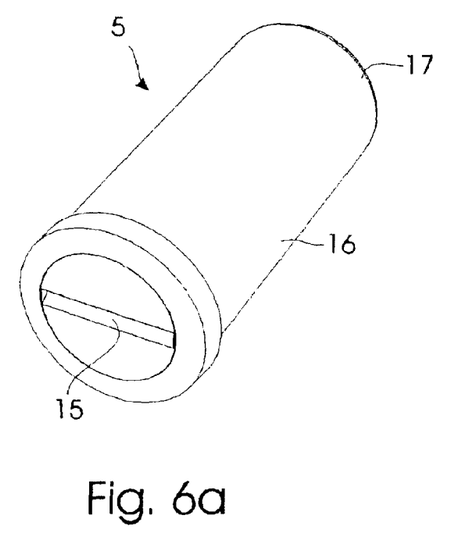

FIGS. 6a,b, and c show in perspective three embodiments of the sealing valve according to the present invention, wherein FIG. 6a illustrates in enlarged scale the embodiment 5 shown in FIG. 1.

Figure 6B:
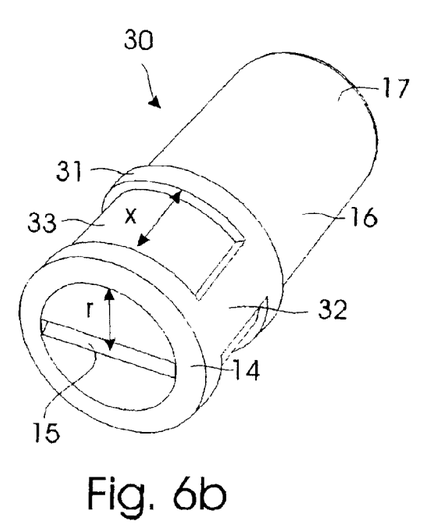

FIG. 6b shows a second exemplary embodiment for a sealing valve 30, which corresponds substantially to the first embodiment 5 shown in FIG. 6a, and for like parts same reference numerals are used. The second embodiment 30 differs from the first embodiment in that the tubular extension 16 is provided with an annular rib 31 and axial ribs 32, of which only one is shown in FIG. 6b. The axial ribs 32 are provided on the exterior face of the tubular extension 16 between the septum seal 14 and the annular rib 31. The ribs 31,32 aid in preventing both unintended rotational and axial displacement to secure the location of the sealing valve 30 inside the catheter hub 2. The axial distance x between the annular rib 31 and the septum seal 14 preferably corresponds to the radius r of the deflectable walls 14a,14b, so that deflection of these walls 14a,14b remains unobstructed when the male luer connector 27 is inserted inside the female proximal end 6.

Figure 7:
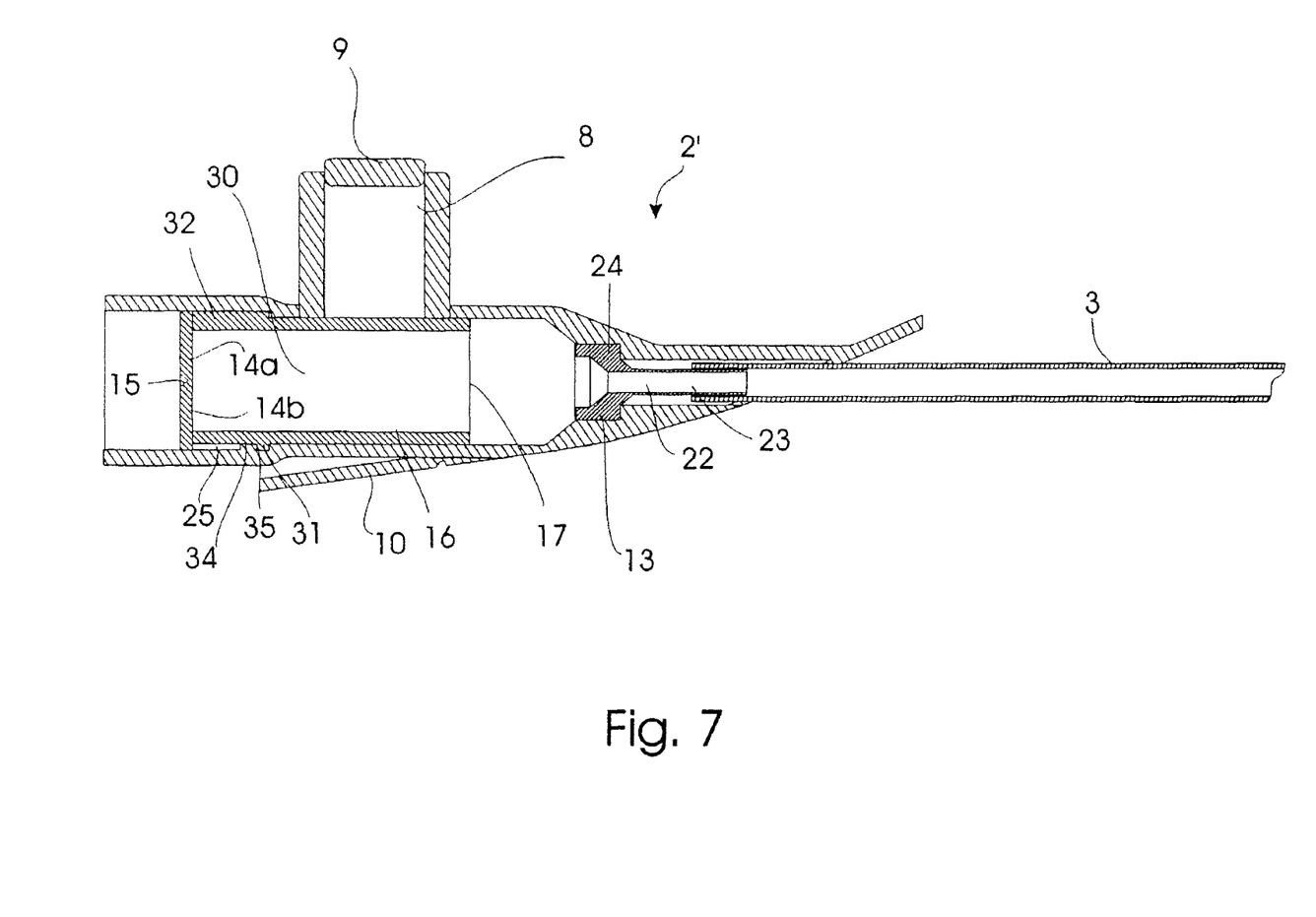
FIG. 7 shows an axial sectional view, similar to that of FIG. 3, but of an alternative embodiment of the catheter hub of the present invention.

In an alternative embodiment 2' of the catheter hub 2, as illustrated in FIG. 7, the recessed annular section 33 of the sealing valve 30 may advantageously be used to receive complementary shaped annular protrusions 34, such as ribs 34, protruding inside the bore 11. Also, the annular rib 31 may be engaged into a complementary shaped recess 35 in the interior wall of the female proximal end 6 of the catheter hub 2'. Hence, no locking ring 12 needs to be used because the sealing valve 30 is held engaged inside the catheter hub by means of the ribs 31,32 and recess 35.

Figure 6C:
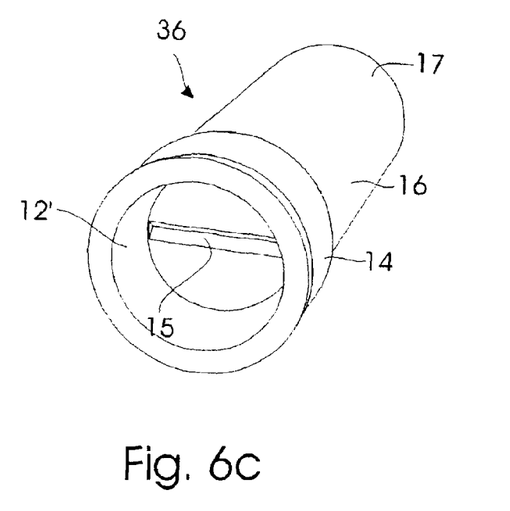

FIG. 6c shows a third exemplary embodiment for a sealing valve 36 which corresponds substantially to the first embodiment 5 shown in FIG. 6a, and for like parts same reference numerals are used. The second embodiment 36 differs from the first embodiment only in that the locking ring 12' is moulded as an integrated part of the sealing valve 36, which can be inserted into the catheter hub 2 or 2' as one single unit.

Figure 8:
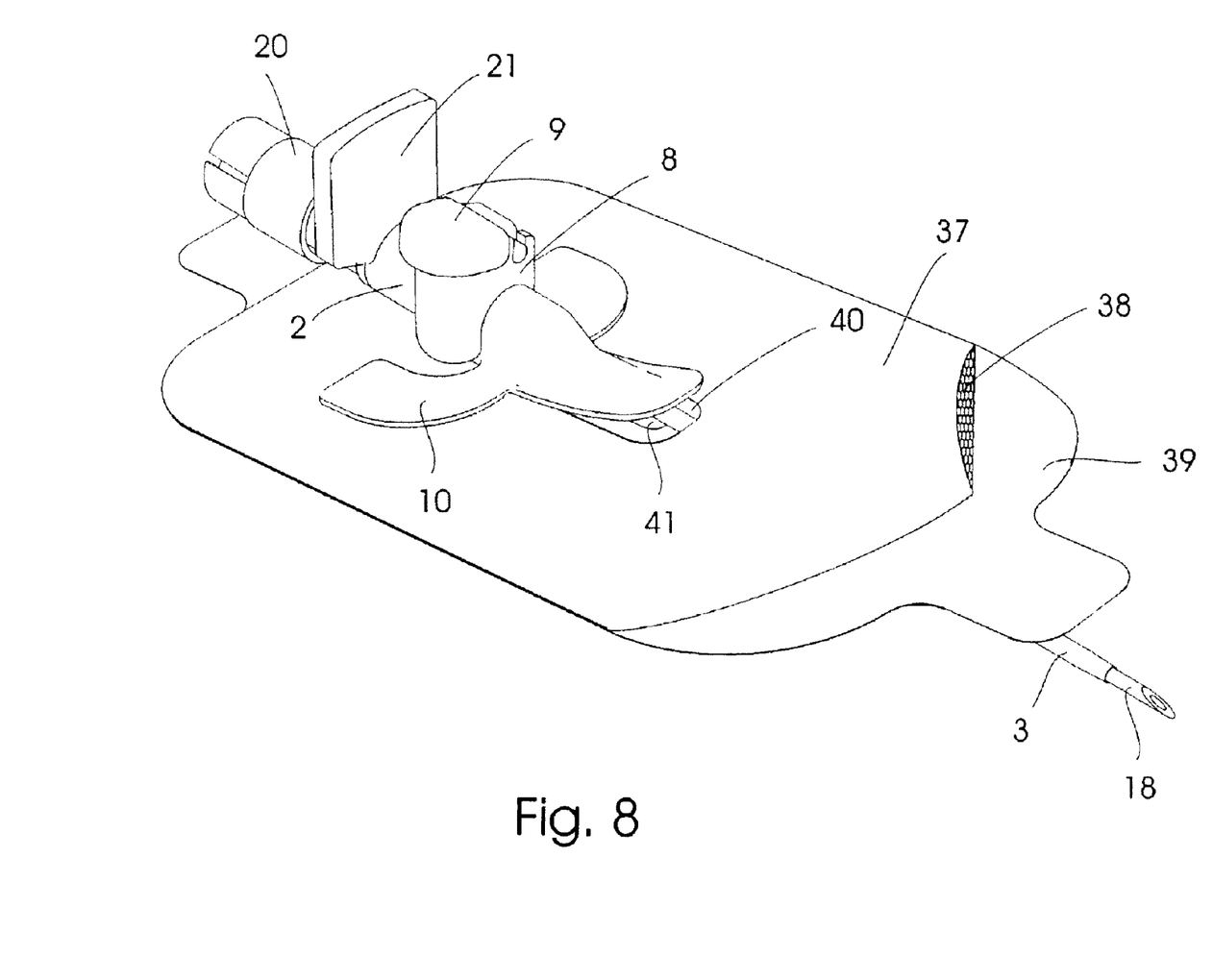
FIG. 8 is a perspective view of a peripheral catheter assembly 1 in which the attachment member is united with a plaster member.

FIG. 8 shows a perspective view of the peripheral catheter assembly 1 in which the attachment member 10 is united with a plaster member 37 for adhering the peripheral catheter assembly 1 to a subjacent surface as (not shown). The plaster member 37 is provided with an adhesive 38, which is protected by a releasable cover sheet 39. The plaster member 37 and the cover sheet 39 have superposing traversing apertures 40,41, respectively, for allowing the catheter tube and needle to pass through when a venipuncture is made.

Although the attachment member 10 is shown to be Y-shaped, any appropriate shape is intended within the scope of the present invention. For example the shape can simply be squared, circular or oval.

The sealing valve according to the present invention provides an efficient self-closing mechanism for a peripheral catheter assembly and constitutes an efficient barrier that assist in preventing contamination, e.g. due to condensation and airborne particles such as mould, spores and dust.

Furthermore, the sealing valve according to the present invention makes venipuncture must easier than hitherto known, providing the physician with a freedom to leave the patient after puncture. No blood flows unintended out of the peripheral catheter when no male part is inserted into the female proximal end and nothing enters inside the body since the female proximal end of the catheter hub always is either sealed or plugged.

What is claimed is:

1. A peripheral catheter assembly comprising:
   a hollow catheter hub having a female proximal end and a distal end provided with a catheter tube,
   at least one infusion port located between the distal and proximal ends,
   a hollow needle module comprising a needle held by a male socket arranged to sealingly engage the female proximal end, and
   a sealing member engaged inside the catheter hub in the form of a sealing valve in the form of a unit piece comprising a septum seal having a weakened portion surrounded by deflectable septum walls, and a hollow tubular extension which protrudes towards a free end from the periphery of the septum seal and extends inside the catheter hub past the infusion port towards the distal end of the catheter hub;
   wherein a portion of the inner periphery of the catheter hub is provided with an annular relief that provides sufficient open space about the septum seal wall and tubular extension for at least partly receiving (1) the deflected septum seal wall or (2) part of the wall of the tubular extension that is displaced outwardly by the deflected septum seal wall due to insertion of the needle module or another male connector into the female proximal end; and
   wherein upon removal of the needle module or male connector from the female proximal end, the sealing member returns to its initial sealing position and remains stationary inside the catheter hub.

2. The peripheral catheter assembly of claim 1, wherein at least the tubular extension is provided with at least one securing means for firmly securing the sealing valve inside the catheter hub to prevent axial displacement of the sealing valve.

3. The peripheral catheter assembly of claim 1, wherein the weakened portion is a notch extending across the septum seal.

4. The peripheral catheter assembly of claim 1, wherein the catheter hub is provided with an attachment member for attaching the peripheral catheter assembly to a subjacent surface.

5. The peripheral catheter assembly of claim 4, wherein the attachment member is united with a plaster member for adhering the peripheral catheter assembly to a subjacent surface, said plaster member has an aperture for passage of at least the catheter tube.

6. The peripheral catheter assembly of claim 1, wherein at least the catheter hub is transparent.

7. A method of using the peripheral catheter assembly according to claim 5, which comprises: folding the part of the plaster member covering the catheter tube back to view the pointed end of the needle, puncturing the vein, advancing the catheter tube into the vein while gradually retracting the needle module until the needle is fully retracted and the septum seal has self-closed, adhering the plaster member to the skin of the patient, establishing fluid connection between the vein and the exterior by inserting a male connector through the septum seal.

8. The method of claim 7, wherein the catheter hub is provided with an annular relief for at least partly receiving the deflected septum seal wall or part of the wall of the tubular extension that is displaced by the deflected septum seal wall when the male connector is inserted.

9. A peripheral catheter assembly comprising:
a hollow catheter hub having a female proximal end and a distal end provided with a catheter tube,
at least one infusion port located between the distal and proximal ends,
a hollow needle module comprising a needle held by a male socket arranged to sealingly engage the female proximal end, and
a sealing member engaged inside the catheter hub in the form of a sealing valve in the form of a unit piece comprising a septum seal having a weakened portion surrounded by deflectable septum walls, and a hollow tubular extension which protrudes towards a free end from the periphery of the septum seal and extends inside the catheter hub past the infusion port towards the distal end of the catheter hub, and
at least one securing means for firmly securing the sealing valve inside the catheter hub to prevent axial and/or rotational displacement of the sealing valve inside the catheter hub;
wherein the catheter hub is provided with an annular relief that provides sufficient open space about the septum seal wall and tubular extension for at least partly receiving (1) the deflected septum seal wall or (2) part of the wall of the tubular extension that is displaced outwardly by the deflected septum seal wall, and
wherein the securing means comprises a circumferential sealing rib and one or more anchoring ribs extending in the axial direction of the tubular extension between the septum seal and the circumferential sealing rib, which ribs are forced fitted into engagement with the female proximal end of the catheter hub.

10. A peripheral catheter assembly comprising:
a hollow catheter hub having a female proximal end and a distal end provided with a catheter tube,
at least one infusion port located between the distal and proximal ends,
a hollow needle module comprising a needle held by a male socket arranged to sealingly engage the female proximal end,
a sealing member engaged inside the catheter hub in the form of a sealing valve in the form of a unit piece comprising a septum seal having a weakened portion surrounded by deflectable septum walls, and a hollow tubular extension which protrudes towards a free end from the periphery of the septum seal and extends inside the catheter hub past the infusion port towards the distal end of the catheter hub, and
a hollow annular locking member having a first end face facing the septum seal and an opposing second free end face with an opening for receiving one of a male socket or a male luer connector;
wherein a portion of the inner periphery of the catheter hub is provided with an annular relief that provides sufficient open space about the septum seal wall and tubular extension for at least partly receiving (1) the deflected septum seal wall or (2) part of the wall of the tubular extension that is displaced outwardly by the deflected septum seal wall due to insertion of the needle module or another male connector into the female proximal end;
wherein upon insertion of the male luer connector, the septum seal fully deflects into the annular recess and opens up to a diameter that is substantially similar diameter to the inner diameter of the catheter hub; and
wherein upon removal of the needle module or male connector from the female proximal end, the sealing member returns to its initial sealing position and remains stationary inside the catheter hub.

11. The peripheral catheter assembly of claim 10, wherein the annular locking member has a bore which tapers towards the first end face of the locking member.

12. A peripheral catheter assembly comprising:
a hollow catheter hub having a female proximal end and a distal end provided with a catheter tube, wherein a portion of the internal periphery of the female proximal end has an internal annular relief,
at least one infusion port located between the distal and proximal ends,
a hollow needle module comprising a needle held by a male socket arranged to sealingly engage the female proximal end, and
a sealing member engaged inside the catheter hub in an initial sealing position and in the form of a sealing valve comprising a septum seal having a weakened portion surrounded by deflectable septum walls, and a hollow tubular extension which protrudes towards a free end from the periphery of the septum seal and extends inside the catheter hub past the infusion port towards the distal end of the catheter hub;
wherein the annular relief provides sufficient open space about the septum seal wall and tubular extension for at least partly receiving (1) the deflected septum seal wall or (2) part of the wall of the tubular extension that is displaced outwardly by the deflected septum seal wall due to insertion of the needle module or another male connector into the female proximal end; and
wherein upon removal of the needle module or male connector from the female proximal end, the sealing member returns to its initial sealing position and remains stationary inside the catheter hub.

13. The peripheral catheter assembly of claim 12, wherein the sealing valve is in the form of a unit piece.

14. The peripheral catheter assembly of claim 12, wherein the hub includes a cylindrical main body, and the annular relief is formed by a portion of the female proximal end of the hub having a larger internal diameter than that of the main body of the hub.

15. A peripheral catheter assembly comprising:
a hollow catheter hub having a female proximal end and a distal end provided with a catheter tube,
at least one infusion port located between the distal and proximal ends,
a hollow needle module comprising a needle held by a male socket arranged to sealingly engage the female proximal end, and
a sealing member engaged inside the catheter hub in the form of a sealing valve in the form of a unit piece comprising a septum seal having a weakened portion surrounded by deflectable septum walls, and a hollow tubular extension which protrudes towards a free end from the periphery of the septum seal and extends inside the catheter hub past the infusion port towards the distal end of the catheter hub;
wherein upon insertion of a male connector into the female proximal end of the hollow catheter hub, the male connector deflects the septum walls into engagement with the interior wall of the female proximal end of the catheter hub, thereby providing a flow path inlet in fluid communication with the vein that has a diameter equal to at least the interior diameter of the male connector; and
wherein upon removal of the needle module or male connector from the female proximal end, the sealing member returns to its initial sealing position and remains stationary inside the catheter hub.

* * * * *